US011125674B2

(12) United States Patent
Rich (10) Patent No.: US 11,125,674 B2
(45) Date of Patent: *Sep. 21, 2021

(54) SYSTEMS AND USER INTERFACE FOR COLLECTING A DATA SET IN A FLOW CYTOMETER

(71) Applicant: Becton, Dickinson and Company, Franklin Lakes, NJ (US)

(72) Inventor: Collin A. Rich, Ann Arbor, MI (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/591,453

(22) Filed: Oct. 2, 2019

(65) Prior Publication Data

US 2020/0088625 A1      Mar. 19, 2020

Related U.S. Application Data

(60) Continuation of application No. 16/015,807, filed on Jun. 22, 2018, now Pat. No. 10,481,074, which is a
(Continued)

(51) Int. Cl.
*G01N 21/59* (2006.01)
*G01N 15/14* (2006.01)
(Continued)

(52) U.S. Cl.
CPC ........ *G01N 15/1434* (2013.01); *G01J 3/0208* (2013.01); *G01J 3/0229* (2013.01);
(Continued)

(58) Field of Classification Search
CPC .......... G06F 19/10; G06F 19/28; G06F 19/26; G06F 19/12; G01N 15/14; G01N 15/1404;
(Continued)

(56) References Cited

U.S. PATENT DOCUMENTS 3,347,273 A   10/1967  Russell
3,601,128 A    8/1971  Hakim
(Continued)

FOREIGN PATENT DOCUMENTS

EP       466490      1/1992
EP       0602416     6/1994
EP       1391611     2/2004
(Continued)

OTHER PUBLICATIONS

Light, 2006, 2 pages. Collins Dictionary of Astronomy. Long, United Kingdom. Retrieved online on Jul. 26, 2015 from http://www.credoreference.com.

*Primary Examiner* — Hoa Q Pham
(74) *Attorney, Agent, or Firm* — Bret E. Field; Bozicevic, Field & Francis LLP (57) ABSTRACT

Systems in a flow cytometer having an interrogation zone and illumination impinging the interrogation zone include: a lens subsystem including a collimating element that collimates light from the interrogation zone, a light dispersion element that disperses collimated light into a light spectrum, and a focusing lens that focuses the light spectrum onto an array of adjacent detection points; a detector array, including semiconductor detector devices, that collectively detects a full spectral range of input light signals, in which each detector device detects a subset spectral range of the full spectral range of light signals; and a user interface that enables a user to create a set of virtual detector channels by grouping detectors in the detector array, such that each virtual detector channel corresponds to a detector group and has a virtual detector channel range including the sum of subset spectral ranges of the detectors in the corresponding detector group.

15 Claims, 5 Drawing Sheets

Related U.S. Application Data continuation of application No. 15/004,521, filed on Jan. 22, 2016, now Pat. No. 10,031,064, which is a division of application No. 13/820,968, filed as application No. PCT/US2011/057747 on Oct. 25, 2011, now Pat. No. 9,280,635.

(60) Provisional application No. 61/406,255, filed on Oct. 25, 2010, provisional application No. 61/406,251, filed on Oct. 25, 2010, provisional application No. 61/406,259, filed on Oct. 25, 2010.

(51) Int. Cl.
| | |
|---|---|
| *G16B 5/00* | (2019.01) |
| *G16B 45/00* | (2019.01) |
| *G16B 99/00* | (2019.01) |
| *G01J 3/18* | (2006.01) |
| *G01J 3/36* | (2006.01) |
| *G01J 3/02* | (2006.01) |
| *G01J 3/28* | (2006.01) |
| *G06M 11/02* | (2006.01) |

(52) U.S. Cl.
CPC ............ *G01J 3/18* (2013.01); *G01J 3/2803* (2013.01); *G01J 3/36* (2013.01); *G01N 15/14* (2013.01); *G01N 15/1404* (2013.01); *G01N 15/1429* (2013.01); *G16B 5/00* (2019.02); *G16B 45/00* (2019.02); *G16B 99/00* (2019.02); *G06M 11/02* (2013.01)

(58) Field of Classification Search
CPC ........... G01N 15/1429; G01N 15/1434; G01N 35/00871; G01N 2015/1006; G01N 2015/1037; G01N 2015/1081; G01N 2015/1087; G01N 2015/1093; G01N 2015/1486; G01N 2015/149; G01N 2015/1493; G01N 2015/1497; G01F 1/00; G01F 25/0007; G06M 11/02
USPC ...... 356/335–343, 73, 246; 702/189, 45, 21, 702/32
See application file for complete search history.

(56) References Cited

U.S. PATENT DOCUMENTS

| | | |
|---|---|---|
| 3,672,402 A | 6/1972 | Bloemer |
| 3,819,272 A | 6/1974 | Crozier et al. |
| 4,112,735 A | 9/1978 | McKnight |
| 4,138,879 A | 2/1979 | Liebermann |
| 4,293,221 A | 10/1981 | Kay et al. |
| 4,371,786 A | 2/1983 | Kramer |
| 4,448,538 A | 5/1984 | Mantel |
| 4,559,454 A | 12/1985 | Kramer |
| 4,570,639 A | 2/1986 | Miodownik |
| 4,691,829 A | 9/1987 | Auer |
| 4,774,189 A | 9/1988 | Schwartz |
| 4,790,653 A | 12/1988 | North, Jr. |
| 4,818,103 A | 4/1989 | Thomas et al. |
| 4,824,641 A | 4/1989 | Williams et al. |
| 4,826,660 A | 5/1989 | Smith et al. |
| 4,844,610 A | 7/1989 | North |
| 4,933,813 A | 6/1990 | Berger |
| 5,028,127 A | 7/1991 | Spitzberg |
| 5,030,002 A | 7/1991 | North |
| 5,040,890 A | 8/1991 | North, Jr. |
| 5,043,706 A | 8/1991 | Oliver |
| 5,055,556 A | 10/1991 | Stryer et al. |
| 5,083,862 A | 1/1992 | Rusnak |
| 5,138,868 A | 8/1992 | Long |
| 5,139,609 A | 8/1992 | Fields et al. |
| 5,150,037 A | 9/1992 | Kouzuki |
| 5,150,313 A | 9/1992 | Vanden et al. |
| 5,155,543 A | 10/1992 | Hirako |
| 5,204,884 A | 4/1993 | Leary et al. |
| 5,224,058 A | 6/1993 | Mickaels et al. |
| 5,270,548 A | 12/1993 | Steinkamp |
| 5,301,685 A | 4/1994 | Guirguis |
| 5,308,990 A | 5/1994 | Takahashi et al. |
| 5,367,474 A | 11/1994 | Auer et al. |
| 5,374,395 A | 12/1994 | Robinson et al. |
| 5,395,588 A | 3/1995 | North et al. |
| 5,403,552 A | 4/1995 | Pardikes |
| 5,466,946 A | 11/1995 | Kleinschmitt |
| 5,469,375 A | 11/1995 | Kosaka |
| 5,539,386 A | 7/1996 | Elliott |
| 5,552,885 A | 9/1996 | Steen |
| 5,559,339 A | 9/1996 | Domanik et al. |
| 5,602,469 A | 2/1997 | Fujii et al. |
| 5,616,124 A | 4/1997 | Hague et al. |
| 5,639,902 A | 6/1997 | Girard et al. |
| 5,684,480 A | 11/1997 | Jansson |
| 5,797,430 A | 8/1998 | Becke et al. |
| 5,798,222 A | 8/1998 | Goix |
| 5,804,507 A | 9/1998 | Perlov et al. |
| 5,883,378 A | 3/1999 | Irish et al. |
| 5,891,734 A | 4/1999 | Gill et al. |
| 5,920,388 A | 7/1999 | Sandberg et al. |
| 5,960,129 A | 9/1999 | Kleinschmitt |
| 5,981,180 A | 11/1999 | Chandler et al. |
| 6,016,376 A | 1/2000 | Ghaemi et al. |
| 6,039,078 A | 3/2000 | Tamari |
| 6,067,157 A | 5/2000 | Altendorf |
| 6,070,477 A | 6/2000 | Mark |
| 6,091,502 A | 7/2000 | Weigl et al. |
| 6,097,485 A | 8/2000 | Lievan |
| 6,110,427 A | 8/2000 | Uffenheimer |
| 6,115,065 A | 9/2000 | Yadid-Pechl et al. |
| 6,154,276 A | 11/2000 | Mariella, Jr. |
| 6,156,208 A | 12/2000 | Desjardins et al. |
| 6,181,319 B1 | 1/2001 | Fukita et al. |
| 6,183,697 B1 | 2/2001 | Tanaka et al. |
| 6,288,783 B1 | 9/2001 | Auad |
| 6,377,721 B1 | 4/2002 | Walt et al. |
| 6,382,228 B1 | 5/2002 | Cabuz et al. |
| 6,403,378 B1 | 6/2002 | Phi-Wilson et al. |
| 6,427,521 B2 | 8/2002 | Jakkula et al. |
| 6,431,950 B1 | 8/2002 | Mayes |
| 6,449,562 B1 | 9/2002 | Chandler et al. |
| 6,456,769 B1 | 9/2002 | Furusawa et al. |
| 6,469,787 B1 | 10/2002 | Meyer et al. |
| 6,473,171 B1 | 10/2002 | Buttry et al. |
| 6,519,355 B2 | 2/2003 | Nelson |
| 6,522,775 B2 | 2/2003 | Nelson |
| 6,587,203 B2 | 7/2003 | Colon |
| 6,636,623 B2 | 10/2003 | Nelson |
| 6,675,835 B2 | 1/2004 | Gerner et al. |
| 6,694,799 B2 | 2/2004 | Small |
| 6,700,130 B2 | 3/2004 | Fritz |
| 6,710,871 B1 | 3/2004 | Goix |
| 6,718,415 B1 | 4/2004 | Chu |
| 6,778,910 B1 | 8/2004 | Vidal et al. |
| 6,809,804 B1 | 10/2004 | Yount et al. |
| 6,816,257 B2 | 11/2004 | Goix |
| 6,825,926 B2 | 11/2004 | Turner et al. |
| 6,852,284 B1 | 2/2005 | Holl et al. |
| 6,859,570 B2 | 2/2005 | Walt et al. |
| 6,869,569 B2 | 3/2005 | Kramer |
| 6,872,180 B2 | 3/2005 | Reinhardt et al. |
| 6,897,954 B2 | 5/2005 | Bishop et al. |
| 6,901,964 B2 | 6/2005 | Kippe et al. |
| 6,908,226 B2 | 6/2005 | Siddiqui et al. |
| 6,912,904 B2 | 7/2005 | Storm, Jr. et al. |
| 6,936,828 B2 | 8/2005 | Saccomanno |
| 6,941,005 B2 | 9/2005 | Lary et al. |
| 6,944,322 B2 | 9/2005 | Johnson et al. |
| 7,009,189 B2 | 3/2006 | Saccomanno |
| 7,012,689 B2 | 3/2006 | Sharpe |
| 7,019,834 B2 | 3/2006 | Sebok et al. |
| 7,024,316 B1 | 4/2006 | Ellison et al. |
| 7,061,595 B2 | 6/2006 | Cabuz et al. |

(56) References Cited

U.S. PATENT DOCUMENTS

| | | | |
|---|---|---|---|
| 7,075,647 B2 | 7/2006 | Christodoulou | |
| 7,105,355 B2 | 9/2006 | Kurabayashi | |
| 7,106,442 B2 | 9/2006 | Silcott et al. | |
| 7,113,266 B1 | 9/2006 | Wells | |
| 7,130,046 B2 | 10/2006 | Fritz et al. | |
| 7,232,687 B2 | 6/2007 | Lary et al. | |
| 7,262,838 B2 | 8/2007 | Fritz | |
| 7,274,316 B2 | 9/2007 | Moore | |
| 7,328,722 B2 | 2/2008 | Rich et al. | |
| 7,362,432 B2 | 4/2008 | Rolh | |
| 7,403,125 B2 | 7/2008 | Rich | |
| 7,471,393 B2 | 12/2008 | Trainer | |
| 7,520,300 B2 | 4/2009 | Rich et al. | |
| 7,628,956 B2 | 12/2009 | Jindo | |
| 7,738,099 B2 | 6/2010 | Morrell et al. | |
| 7,776,268 B2 | 8/2010 | Rich | |
| 7,780,916 B2 | 8/2010 | Bair et al. | |
| 7,843,561 B2 | 11/2010 | Rich | |
| 7,857,005 B2 | 12/2010 | Rich et al. | |
| 7,903,706 B2 | 3/2011 | Oshaughnessy | |
| 7,981,661 B2 | 7/2011 | Rich | |
| 7,996,188 B2 | 8/2011 | Olson et al. | |
| 8,017,402 B2 | 9/2011 | Rich | |
| 8,031,340 B2 | 10/2011 | Rich et al. | |
| 9,194,785 B2 | 11/2015 | Bentien | |
| 9,280,635 B2 * | 3/2016 | Rich | G01N 15/1404 |
| 9,551,600 B2 * | 1/2017 | Howes | G06F 17/00 |
| 10,031,064 B2 * | 7/2018 | Rich | G01J 3/36 |
| 10,481,074 B2 * | 11/2019 | Rich | G01N 15/14 |
| 2001/0014477 A1 | 8/2001 | Pelc et al. | |
| 2001/0039053 A1 | 11/2001 | Liseo et al. | |
| 2002/0028434 A1 | 3/2002 | Goix et al. | |
| 2002/0059959 A1 | 5/2002 | Quatu et al. | |
| 2002/0080341 A1 | 6/2002 | Kosaka | |
| 2002/0098115 A1 | 7/2002 | Fawcett et al. | |
| 2002/0123154 A1 | 9/2002 | Burshleyn et al. | |
| 2002/0192113 A1 | 12/2002 | Uffenheimer | |
| 2003/0048539 A1 | 3/2003 | Oostman et al. | |
| 2003/0054558 A1 | 3/2003 | Kurabayashi | |
| 2003/0062314 A1 | 4/2003 | Davidson et al. | |
| 2003/0072549 A1 | 4/2003 | Facer et al. | |
| 2003/0078703 A1 | 4/2003 | Potts et al. | |
| 2003/0129090 A1 | 7/2003 | Farrell | |
| 2003/0134330 A1 | 7/2003 | Ravkin et al. | |
| 2003/0148379 A1 | 8/2003 | Roitman et al. | |
| 2003/0175157 A1 | 9/2003 | Micklash et al. | |
| 2003/0202175 A1 | 10/2003 | Van Den et al. | |
| 2003/0211009 A1 | 11/2003 | Buchanan | |
| 2004/0031521 A1 | 2/2004 | Vrane et al. | |
| 2004/0048362 A1 | 3/2004 | Trulson et al. | |
| 2004/0112808 A1 | 6/2004 | Takagi et al. | |
| 2004/0119974 A1 | 6/2004 | Bishop et al. | |
| 2004/0123645 A1 | 7/2004 | Storm et al. | |
| 2004/0143423 A1 | 7/2004 | Parks et al. | |
| 2004/0175837 A1 | 9/2004 | Bonne et al. | |
| 2004/0197768 A1 | 10/2004 | Glenncross | |
| 2004/0201845 A1 | 10/2004 | Quist et al. | |
| 2005/0047292 A1 | 3/2005 | Parks et al. | |
| 2005/0057749 A1 | 3/2005 | Dietz et al. | |
| 2005/0069454 A1 | 3/2005 | Bell | |
| 2005/0073686 A1 | 4/2005 | Roth | |
| 2005/0078299 A1 | 4/2005 | Fritz et al. | |
| 2005/0105091 A1 | 5/2005 | Lieberman et al. | |
| 2005/0162648 A1 | 7/2005 | Auer et al. | |
| 2005/0163663 A1 | 7/2005 | Martino et al. | |
| 2005/0195605 A1 | 9/2005 | Saccomanno | |
| 2005/0195684 A1 | 9/2005 | Mayer | |
| 2005/0252574 A1 | 11/2005 | Khan et al. | |
| 2005/0275839 A1 | 12/2005 | Robinson et al. | |
| 2006/0002634 A1 | 1/2006 | Riley et al. | |
| 2006/0015291 A1 | 1/2006 | Parks et al. | |
| 2006/0023219 A1 | 2/2006 | Meyer et al. | |
| 2006/0177937 A1 | 8/2006 | Kurabayashi | |
| 2006/0219873 A1 | 10/2006 | Martin et al. | |
| 2006/0273260 A1 | 12/2006 | Casstevens | |
| 2006/0280061 A1 | 12/2006 | Koreeda et al. | |
| 2006/0281143 A1 | 12/2006 | Liu et al. | |
| 2006/0286549 A1 | 12/2006 | Sohn et al. | |
| 2007/0003434 A1 | 1/2007 | Padmanabhan | |
| 2007/0041013 A1 | 2/2007 | Fritz et al. | |
| 2007/0059205 A1 | 3/2007 | Ganz et al. | |
| 2007/0079653 A1 | 4/2007 | Zuleta et al. | |
| 2007/0096039 A1 | 5/2007 | Kapoor et al. | |
| 2007/0124089 A1 | 5/2007 | Jochum et al. | |
| 2007/0127863 A1 | 6/2007 | Bair et al. | |
| 2007/0144277 A1 | 6/2007 | Padmanabhan | |
| 2007/0212262 A1 | 9/2007 | Rich | |
| 2007/0224684 A1 | 9/2007 | Olson et al. | |
| 2007/0243106 A1 | 10/2007 | Rich | |
| 2008/0010019 A1 | 1/2008 | Thomas et al. | |
| 2008/0064113 A1 | 3/2008 | Goix et al. | |
| 2008/0092961 A1 | 4/2008 | Bair et al. | |
| 2008/0215297 A1 | 9/2008 | Goebel et al. | |
| 2008/0228444 A1 | 9/2008 | Olson et al. | |
| 2008/0240539 A1 | 10/2008 | George et al. | |
| 2008/0246949 A1 | 10/2008 | Harris et al. | |
| 2009/0104075 A1 | 4/2009 | Rich | |
| 2009/0174881 A1 | 7/2009 | Rich | |
| 2009/0201501 A1 | 8/2009 | Bair et al. | |
| 2009/0202130 A1 | 8/2009 | George et al. | |
| 2009/0216478 A1 | 8/2009 | Estevez-Labori | |
| 2009/0257339 A1 | 10/2009 | Katayama | |
| 2009/0260701 A1 | 10/2009 | Rich et al. | |
| 2009/0276186 A1 | 11/2009 | Salinas et al. | |
| 2009/0293910 A1 | 12/2009 | Ball et al. | |
| 2010/0008204 A1 | 1/2010 | Bae et al. | |
| 2010/0096560 A1 | 4/2010 | Imanishi | |
| 2010/0118298 A1 | 5/2010 | Bair et al. | |
| 2010/0119298 A1 | 5/2010 | Huang | |
| 2010/0120059 A1 | 5/2010 | Yan et al. | |
| 2010/0302536 A1 | 12/2010 | Ball et al. | |
| 2010/0319469 A1 | 12/2010 | Rich | |
| 2010/0319786 A1 | 12/2010 | Bair et al. | |
| 2011/0058163 A1 | 3/2011 | Rich | |
| 2011/0061471 A1 | 3/2011 | Rich et al. | |
| 2011/0306031 A1 | 12/2011 | Rich | |

FOREIGN PATENT DOCUMENTS

| | | |
|---|---|---|
| EP | 196736 | 3/2004 |
| EP | 1521076 | 4/2005 |
| JP | 356169978 | 12/1981 |
| JP | 5913689 | 3/1984 |
| JP | 6353901 | 4/1988 |
| JP | 0486546 | 3/1992 |
| JP | 6194299 | 7/1994 |
| JP | 06221988 | 12/1994 |
| JP | 7260084 | 10/1995 |
| JP | 08201267 | 8/1996 |
| JP | 09288053 | 11/1997 |
| JP | 10227737 | 8/1998 |
| JP | 2001050887 | 2/2001 |
| JP | 2001170062 | 6/2001 |
| JP | 2003262201 | 9/2003 |
| JP | 200477484 | 3/2004 |
| JP | 4065654 | 3/2008 |
| JP | 2008197043 | 8/2008 |
| WO | WO199915905 | 4/1999 |
| WO | WO1999056052 | 11/1999 |
| WO | WO2001094914 | 12/2001 |
| WO | WO2004003504 | 1/2004 |
| WO | WO2005017499 | 2/2005 |
| WO | WO2005068971 | 7/2005 |
| WO | WO2005073694 | 8/2005 |
| WO | WO200598379 | 10/2005 |
| WO | WO2005091893 | 10/2005 |
| WO | WO2006055772 | 5/2006 |
| WO | WO2007067577 | 6/2007 |
| WO | WO2007100723 | 9/2007 |
| WO | WO2007136749 | 11/2007 |
| WO | WO2008058217 | 5/2008 |
| WO | WO2010063455 | 6/2010 |

* cited by examiner

$\lambda_1 = \lambda_x - \lambda_y$, etc.

SYSTEMS AND USER INTERFACE FOR COLLECTING A DATA SET IN A FLOW CYTOMETER

CROSS-REFERENCE TO RELATED APPLICATIONS

This application is a divisional prior U.S. application Ser. No. 13/820,968, filed 4 Apr. 2013, which is a 371 of PCT/US11/577,747, filed 25 Oct. 2011, which claims the benefit of U.S. Provisional Application Nos. 61/406,251, filed 25 Oct. 2010, 61/406,255, filed 25 Oct. 2010, and 61/406,259, filed 25 Oct. 2010, which are each incorporated in its entirety by this reference.

TECHNICAL FIELD

This invention relates generally to the flow cytometer field, and more specifically to a new and useful systems and user interface in the flow cytometry field.

BACKGROUND

In a flow cytometer, light is directed onto a stream of sample fluid such that the light impinges and typically excites particles in the sample, causing the excited particles to emit light. The detection of the emitted light provides data that can be analyzed for characterizing the particles and the sample fluid, such as count, physical structure, chemical structure, and other useful information in applications such as for research and clinical purposes. The detection system is therefore a crucial component of a flow cytometer and is a factor in not only the quality (e.g., sensitivity, bandwidth) of the collected data, but also the overall structure and cost of the complete flow cytometer system. In conventional flow cytometers, the detection system includes photomultiplier tubes, or PMTs, which have relatively high sensitivity and high bandwidth, and produces data with relatively low noise. However, PMTs have several disadvantages, such as being relatively expensive and exhibiting temperature drift.

Furthermore, a typical flow cytometer detector has a limited collection range. In simple terms, the collection range of a typical flow cytometer is smaller than the signal range of the objects being analyzed with the flow cytometer. For this reason, the typical detector is supplied with a gain level and/or amplifier. Detectors typically collect data relative to an object's size (light scatter) or brightness (fluorescence); both types of data are often collected on each object detected in the sample. To collect signals from small or faint objects, the gain level is increased. With an increased gain level, however, the signals from large or bright objects are too intense to be collected. To collect signals from large or bright objects, the gain level is decreased. With a decreased gain level, however, the signals from small or faint objects are too weak to be collected. The setting of gain level and other parameters is complicated and difficult. The limitations of the user interface of typical flow cytometer systems have several disadvantages, including: (1) the expenditure of valuable user time spent on the gainsetting process to ensure it is set correctly; (2) the requirement of significantly more sample to determine the proper gain settings; (3) the potential loss of valuable data because at least a portion of input signals are outside of the user-set "active" dynamic collection range and are therefore not collected, and (4) the inability to observe and "undo" changes in user-set gain/ scaling settings without running additional samples.

The use of detectors in flow cytometers is also complicated by complex optical systems. To use a conventional optical system, beam splitters and filters must be arranged in a very particular order to properly direct light of particular wavelengths to the appropriate detectors. Rearrangement of the optical system is required whenever a different wavelength detection configuration is required, such as experiments or tests using different fluorochromes. A user must skillfully perform this rearrangement, or the detector system will not function correctly. This limitation prevents the easy swapability of the filters and the easy modification of detection parameters. Further, the particular arrangement of the optical system decreases the reliability and the ruggedness of the flow cytometers, since alignment of the various optical components affects the operability of the detection system.

Thus, there is a need in the flow cytometry field to create new and useful systems and user interface. This invention provides such new and useful systems and user interface for collecting a data set in a flow cytometer.

BRIEF DESCRIPTION OF THE FIGURES

FIGS. 5A-5E are schematics of variations of a method for collecting a data set, enabled by the user interface of the first preferred embodiment; and FIGS. 6A-6F are schematics of variations of a method for collecting a data set, enabled by the user interface of the second preferred embodiment.

DESCRIPTION OF THE PREFERRED EMBODIMENTS

The following description of preferred embodiments of the invention is not intended to limit the invention to these preferred embodiments, but rather to enable any person skilled in the art to make and use this invention.

Figure 1:
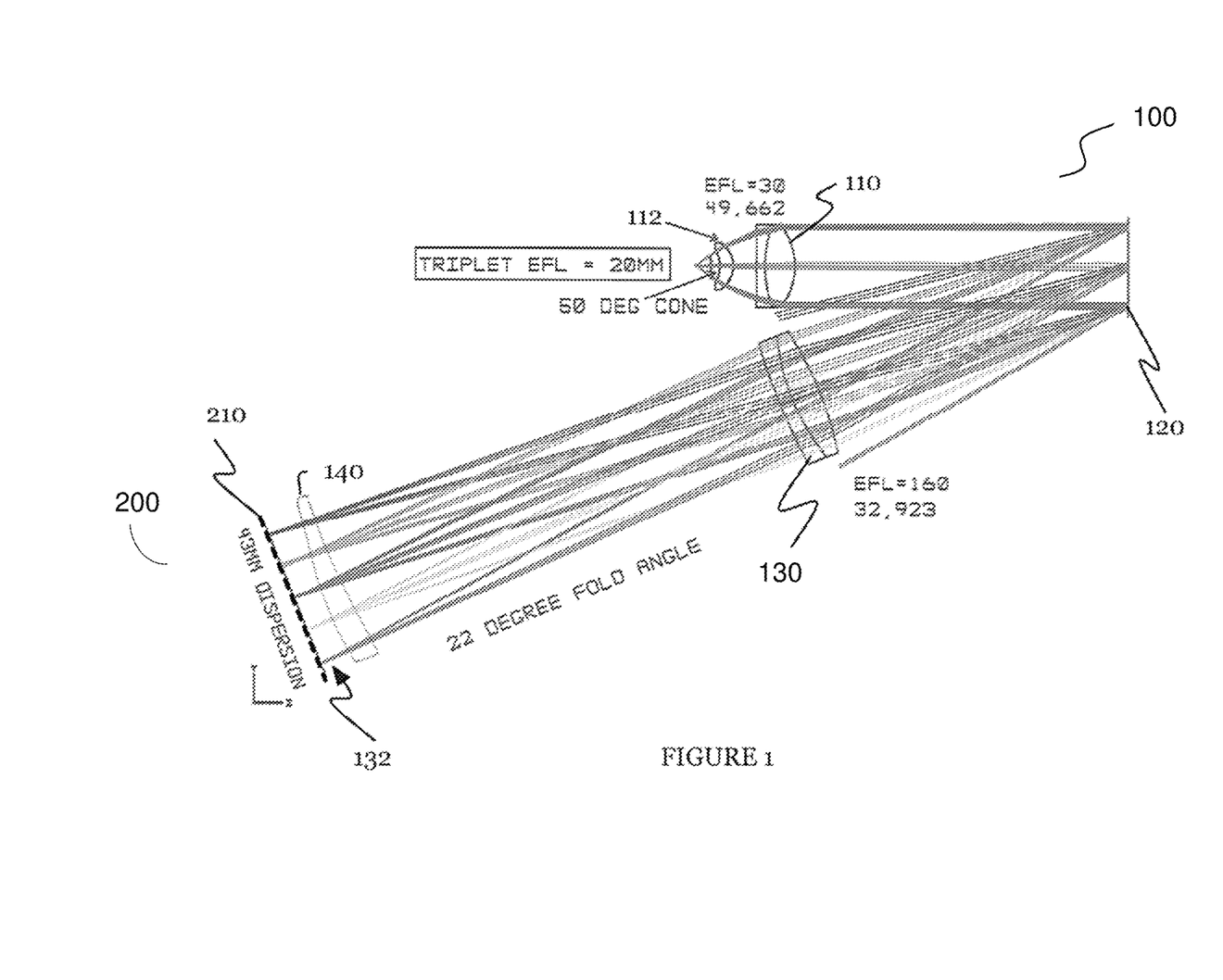
FIG. 1 is a schematic of the optical system of a preferred embodiment.

In a preferred embodiment, systems for collecting a data set in a flow cytometer include optical and detection systems in a flow cytometer 102 having a flow channel with an interrogation zone and an illumination source that impinges the interrogation zone from a particular direction. As shown in FIG. 1, the optical system 100 preferably includes a lens subsystem including a collimating element that receives and collimates light from the interrogation zone, a light dispersion element that disperses the collimated light into a continuous wavelength spectrum of light, and a focusing lens that focuses light spectrum onto an array of adjacent detection points. The detection system 200 for a flow cytometer includes at least one semiconductor detector device that detects the focused light at a detection point and produces a signal corresponding to the detected light; a low noise amplifier circuit that amplifies the signal and is characterized by a high gain-bandwidth product; and a noise filter that reduces electronic noise from the amplified signal. The detection system 200 preferably includes multiple such detectors in a detector array that collectively detects a full spectral range of input signals from the flow cytometer, in which each detector detects a subset spectral range of the full spectral range. The user interface of a preferred embodiment enables a user to create a set of virtual detector channels by grouping detectors in the detector array, such that each virtual detector channel corresponds to a detector group and has a virtual detector channel range including the sum of subset spectral ranges of the detectors in the corresponding detector group. user interface of the preferred embodiments eliminate the discrete and complex system of detectors and filters used in conventional flow cytometers, thereby simplifying The systems and the overall flow cytometer system and enabling a more compact, easier to use flow cytometer. The optical and detection systems also capture all usable light, thereby increasing the power and usability of the flow cytometer. Although the optical and detection systems and user interface are preferably integrated in a flow cytometer, the systems and user interface may alternatively be used in microscopy and/or any suitable apparatus or application for collecting and detecting light.

Optical System

As shown in FIG. 1, the optical system 100 preferably includes a lens subsystem including a collimating element 110 that receives and collimates light from the interrogation zone, a light dispersion element 120 that disperses the collimated light into a continuous wavelength spectrum of light, and a focusing lens 130 that focuses light spectrum onto an array of adjacent detection points 132, such that a detector array may collect the focused light at the adjacent detection points 132. The optical system 100 may further include a clean-up element that reduces spurious reflections and/or other undesired optical artifacts. In one embodiment, the optical system 100 receives and directs light towards a detection system that includes photodiode light detectors, but may alternatively receive and direct light toward a detection system that includes phototransistor light detectors, or any suitable detector.

The lens subsystem includes multiple lens and/or lens surfaces that function to manipulate the light from the illumination source into a form and/or to detection point locations where the light is detectable by a detector array. In a first stage of the lens subsystem, the collimating element 110 is preferably a collimating lens that aligns light from the interrogation zone, and more preferably an achromatic doublet lens, but may include any suitable combination of lenses or other collimating element. The collimating element 110 preferably perfectly or near-perfectly collimates the light into substantially parallel light rays, since the effects of imperfect collimation appear at subsequent stages of the lens subsystem, resulting in poorly-focused light at the detection points 132 and thereby degrading the detection of the light originating from the interrogation zone. As shown in FIG. 1, the collimating element 110 may be coupled to or otherwise optically paired with an aplanatic meniscus lens 112. The pairing of the collimating element 110 and aplanatic meniscus lens 112 increases the effective numerical aperture of the first stage of the lens subsystem, thereby increasing the overall efficiency of light collection from the interrogation zone. The pairing also reduces the overall focal length of the first stage of the lens subsystem, without introducing additional undesirable spherical aberrations or other optical aberrations, which enables the lens subsystem to be made more compact. In one exemplary embodiment, the collimating element 110 is an achromatic doublet lens with an effective focal length of approximately 30 millimeters and the aplanatic meniscus lens has an approximately 50 degree cone, such that the triplet lens combination of the collimating element and meniscus lens has an effective focal length of approximately 20 millimeters.

In a second stage of the lens subsystem, the light dispersion element 120 functions to disperse the collimated light from the collimating element 110 into a continuous wavelength spectrum of light. The light dispersion element 120 is preferably mounted in alignment with the output of the collimating element, such as in a frame, and may be permanently fixed or adjustable in position relative to the collimating element. As shown in FIG. 1, after passing through the light dispersion element 120, the light is preferably redirected such that light rays of the same wavelength are parallel and light rays of different wavelengths are nonparallel at relative angles corresponding to their relative position in the wavelength spectrum. The light dispersion element 120 is preferably one of multiple variations. In a first variation, the light dispersion element 120 includes a diffraction grating that splits and diffracts light into a continuous spectrum of light rays towards the third stage of the lens subsystem. In a second variation, the light dispersion element 120 includes a dispersive prism that breaks up the collimated light into a continuous spectrum of light rays towards the third stage of the lens subsystem. In either variation, the dispersed light may follow a fold angle that is an acute angle, which may enable a more compact lens subsystem, or any suitable angle. In an exemplary embodiment, the light dispersion element 120 is a diffraction grating or prism with a grating of approximately 600 lines/millimeter, and the light dispersion element provides a fold angle of approximately 22 degrees. However, the light dispersion element may include any suitable structure with any suitable level of grating and/or fold angle.

In a third stage of the lens subsystem, the focusing lens 130 functions to focus the dispersed, continuous spectrum of light onto an array of adjacent detection points 132. As shown in FIG. 1, the focusing lens 130 preferably gathers light of similar wavelength together such that all light focused on the array of detection points 132 is arranged in spectral order, but the dispersed light may be focused in any suitable manner. For example, beam splitters or additional stages in the lens subsystem may redirect selected spectral portions of the dispersed light to be arranged in any suitable spectral order, and/or focus selected spectral portions of the dispersed light onto detection points in any suitable location. Each detection point 132 may have a spot size of approximately 0.8 mm2, or any suitable spot size. The array of detection points 132 is preferably a linear array. For instance, light corresponding to shorter wavelengths is preferably focused near a first end of the array of detection points 132, and light corresponding to longer wavelengths is preferably focused near a second end of the array of detection points 132, opposite the first end. However, the array of detection points may alternatively be an arcuate array (e.g., an open arc segment or enclosed circle or ellipse) or any suitable shape. In an exemplary embodiment, the focusing lens 130 has an effective focal length of approximately 160 millimeters and focuses the light to a linear array of detection points covering a dispersion distance of approximately 43 millimeters long. However, the focusing lens may be any suitable lens or lens surface, and may focus the light to any suitable arrangement of detection points.

In some embodiments, the optical system 100 may further include a cleanup element 140 that functions to reduce undesired optical artifacts or other aspects of the received light, such as crosstalk from spurious grating reflections. In one variation, the clean-up element 140 includes an optical filter. For example, the optical filter may be continuously variable, segmented, upper half, lower half, or any suitable type of filter. The filter may additionally and/or alternatively block one or more specific wavelengths from reaching the array of detector points 132, such as the wavelength of a laser or lasers used to excite fluorescent particles in the interrogation zone. For example, such a blocking filter may include an optical notch filter, or a thin blocking bar that positioned at a particular detection point to absorb a particular wavelength or mask the detector from receiving light of the particular wavelength at the detection point, but the blocking filter may additionally and/or alternatively include any suitable filtering device. In another variation, the clean-up element 140 includes a slit grid, which may include any suitable slit grid known to one ordinarily skilled in the art or other suitable slit grid. The optical system may include any suitable number of clean-up elements 140. One or more clean-up elements 140 may be positioned after the light dispersion stage of the lens subsystem and before or after the focusing stage of the lens subsystem, or in any suitable portion of the lens subsystem.

Detection System

Figure 2:
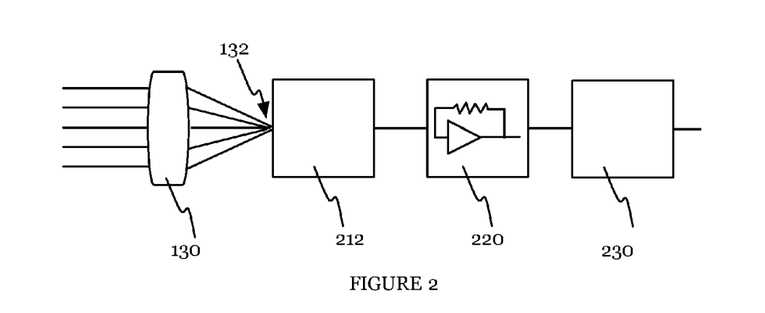
FIG. 2 is a schematic of a signal processing circuit for the detection system of a preferred embodiment.

The detection system 200 preferably includes one or more semiconductor light detector devices 212 in a detector array 210. Each semiconductor detector device 212 detects the light at a respective detection point 132 (focused by the optical system 100 described above, or any suitable optical system) and produces an electrical signal corresponding to the detected light. As shown in FIG. 2, the detection system 200 preferably further includes signal processing circuitry including: a low noise amplifier circuit 220 that boosts or amplifies the signal from the detector device 212 and that is characterized by a high gain-bandwidth product; and a noise filter 230 that reduces electronic noise from the amplified signal.

The semiconductor detector device 212 functions to convert light into an electrical signal having characteristics that correlate with the nature of the light received from the interrogation zone. The wavelength sensitivity of the detector device 212 is preferably optimized to detect light between a full range of approximately 400 nanometers and g00 nanometers in wavelength, either a subset of the full range or over the entire full range. Furthermore, the wavelength sensitivity of the detector device 212 may be optimized to minimize detection of light in the infrared range, such as to avoid responding to sources of heat in the flow cytometer or other instrument in which the detection system is integrated. However, the detector devices may be optimized to detect any suitable range of wavelengths of light.

The angular sensitivity of the semiconductor detector device 212 may be optimized to receive light in a cone approximately corresponding to the focused cone of light emanating from the light focusing element of the optical system described above, while rejecting stray light passing outside of the cone, which may thereby minimize sensitivity to light traveling off-axis within the optical system. Furthermore, the semiconductor detector device 212 may be shielded from any backlight or other ambient light sources to minimize background noise in the signal and improve the accuracy of the resulting collected data set from the flow cytometer (or other instrument). The semiconductor device 212 may additionally and/or alternatively be shielded from electromagnetic fields to minimize induced electronic noise. Furthermore, the semiconductor detector device 212 may include temperature compensation to minimize any temperature-induced changes in gain or linearity of the output signal.

The semiconductor detector device 212 may be any suitable semiconductor device or light detector device. In a preferred variation, the semiconductor detector device 212 is a photodiode, and more preferably a PIN photodiode, although the photodiode may be any suitable kind of diode. The photodiode preferably has a very low capacitance, such as approximately 20 pF or less. Since photodiodes with low capacitance are generally physically smaller and have a smaller light-sensitive region, the photodiode detector devices 212 are preferably placed at detection points 132 at which light is well-focused, such as by the optical system described above or any suitable optical system. The photodiode is preferably configured to output current that correlates with characteristics of the received light, but may alternatively be configured to output another suitable electrical characteristic, such as voltage.

In an alternative variation, the semiconductor detector device 212 is a phototransistor. Like the photodiode of the preferred variation, the phototransistor preferably has a very low capacitance and may have a small light-sensitive region such that the phototransistor requires placement at a detection point receiving well-focused light. The phototransistor may be configured to provide an output signal having a substantially linear gain response across the intended light power range of the input signals, such as by applying a suitable current bias to the base of the phototransistor, typically in the range of approximately 10 μm to 1 mA. Furthermore, the output signal from the phototransistor may be converted from a current signal to a voltage signal, such as by feeding the output signal into the low-noise amplifier circuit, a load resistor or other suitable circuitry components. In some embodiments, the phototransistor may provide additional current gain that may be leveraged to increase gain of the signal and/or increase the signal-to-noise ratio. In particular, the use of a phototransistor may reduce the required resistance value of the gain resistor in the amplifier circuit, and consequently may reduce the thermal noise contribution to overall detector noise.

The low-noise amplifier circuit 220 functions to convert current input from the semiconductor detector device 212 to a voltage output and to amplify the signal from the semiconductor detector device 212. The low-noise amplifier circuit 220 preferably includes a transimpedance amplifier, but may be any suitable kind of amplifier. The amplifier circuit preferably has a high open-loop gain-bandwidth product, such as approximately 1 GHz or more. The combination of a semiconductor detector device 212 having low capacitance and a transimpedance amplifier having a high gain-bandwidth product may enable the detection system 200 to have high gain (to amplify the signal from the detector) while maintaining high sensitivity and high bandwidth. The amplifier circuit 220 may further be characterized with a high feedback resistance, low voltage noise and low current noise to reduce overall noise in the signal, and low input capacitance. In an exemplary embodiment, the transimpedance amplifier has a feedback resistance between 1-20 MOhms and preferably more than approximately 10 MOhms, voltage noise of less than approximately 5 n V/rtHz, current noise of less than approximately 5 fA/rtHz, and input capacitance less than approximately 6 pF. However, other embodiments of the amplifier circuit may have any suitable specifications. The amplifier circuit 220 may additionally and/or alternatively include any suitable electronic components that perform current-to-voltage conversion, or the detection system may include any suitable conversion circuitry (e.g., a passive current-to-voltage converter). The amplifier circuit may additionally and/or alternatively include digital signal processing.

The noise filter 230 functions to reduce electronic noise and/or photoinduced noise from the amplified signal, thereby increasing the signal-to-noise ratio. The noise filter 230 may include a low pass filter that quickly attenuates higher frequency noise above a predetermined cutoff point. The noise filter 230 may be implemented in hardware circuitry and/or digitally. In an exemplary embodiment, the low pass filter includes 120 dB or better attenuation, preferably with a 500 kHz or smaller transition band. The noise filter may additionally and/or alternatively include further signal processing techniques such as a smoothing algorithm.

Figure 3:
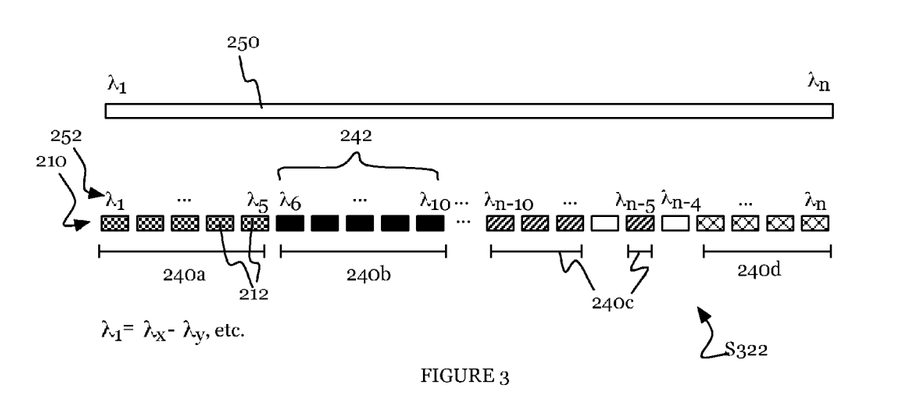
FIG. 3 is a schematic of the detection system and virtual detector channels of preferred embodiments.

As shown in FIG. 3, in a preferred embodiment, the detection system 200 preferably includes multiple semiconductor light detector devices 212 in a detector array 210 that collectively detects a full spectral range 250 of input signals from the flow cytometer, and in which each detector detects a subset spectral range 252 of the full spectral range. However, the semiconductor detector device 212 (e.g. photodiode or photo transistor) may alternatively be used in any suitable detection system. In an exemplary embodiment, the detection system detects a full spectral range 250 of input signals of approximately 400-900 nm, but may alternatively detect any suitable spectral range of light. Overall, the detection system 200 preferably is configured to have a bandwidth of at least approximately 400 kHz. However, in some embodiments, such as for use in flow cytometers having frequency modulated lasers at light sources in the interrogation zone, the detection system 200 may have a bandwidth of at least approximately 2 MHz. Alternatively, the detection system 200 may have any suitable bandwidth. Furthermore, the detector array 210 preferably detects a wide range of input signals that includes at least a 1:100,000 ratio, and more preferably at least a 1:1,000,000 ratio, between the faintest objects and the brightest objects. In a preferred embodiment, the detector array 210 is a linear array, such that a dispersed spectrum of light may be incident on the detector array, with light of shorter wavelengths detected near a first end of the linear array and light of longer wavelengths detected near a second end of the linear array opposite the first end. Alternatively, the detector array 210 may be an arcuate array (e.g., an open arc segment or enclosed circle or ellipse) or any suitable shape, preferably with adjacent and contiguous detector devices 212.

Each detector device 212 in the detector array 210 preferably detects a respective portion or subset of the full spectral range 250 of the detection system 200. In particular, the detector array 210 is preferably capable of detecting a continuous spectral range of light, and each detector device 212 may be configured to detect a subset spectral range based on its individual characteristics, and/or by its relative position in the detector array 210. For example, the detector array 210 may include 50 detectors that each detects light of approximately 10 nm wavelength increments, from approximately 400-900 nm. The subset spectral ranges 252 of the detectors 212 may be of equal span (e.g. each detector detects, as a result of capability and/or respective position in the detector array, a subset range of 10 nm in the full spectral range), or may be of unequal span. In some embodiments, some or all of the detectors may detect light of overlapping spectra. For example, one detector may detect light of 510-530 nm, and an adjacent detector may detect light of 520-540 nm, such that the two adjacent detectors both detect light of 10 nm (520-530 nm). However, the detector array 210 may include any suitable number of detectors, and the detectors may detect any suitable wavelength ranges of light and/or overlapping wavelength ranges of light. The "spillover" spectral overlap resulting from detection of a particular wavelength of light by multiple detectors may be automatically compensated by techniques known and used by one ordinarily skilled in the art, compensated by user-controlled techniques, and/or any suitable compensation methods. Although the detector array 210 preferably detects a continuous spectral range of light, the detector array may alternatively detect a discontinuous spectral range of light, or selected subsets of the full spectral range 250 of light.

As shown in FIG. 3, individual detectors may be grouped into virtual detector channels 240a, 240b, 240c and 240d, and/or actual detector channels, through which the data set from the flow cytometer or other instrument may be collected. Each virtual detector channel 240a, 240b, 240c and 240d corresponds to a detector group and has a virtual detector channel range 242 that includes the sum of the subset spectral ranges 252 of the detectors in the corresponding detector group. In other words, each virtual detector channel 240a, 240b, 240c and 240d includes the summed or combined input signals collectively detected by the individual detectors 212 in the detector group corresponding to the virtual detector channel 240a, 240b, 240c or 240d. Some or all of the virtual detector channels may include substantially equal virtual detector channel ranges or unequal virtual detector channel ranges. In particular, the detectors may be grouped in a first configuration corresponding to a first set of virtual detector channels and in a second configuration corresponding to a second set of virtual detector channels, where the first and second configurations are different. In other words, the grouping of signals from the detectors may be arranged and repeatedly rearranged in different groups between uses and applications, without requiring physical rearrangement of the components of the optical system and detection system.

User Interface

Figure 4A:
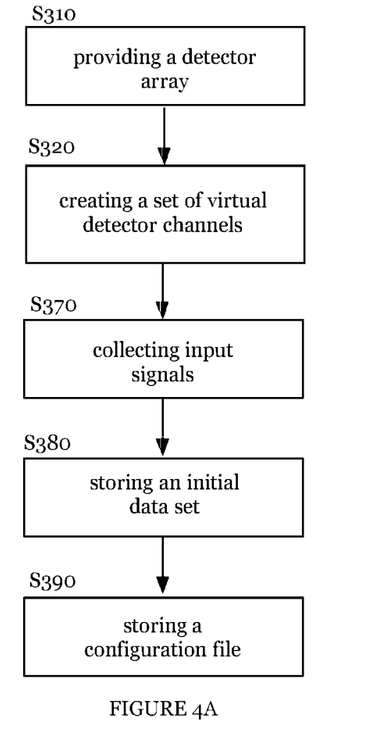
FIGS. 4A and 4B are flowcharts of a method for collecting a data set, enabled by the user interface of first and second preferred embodiments, respectively.
Figure 4B:
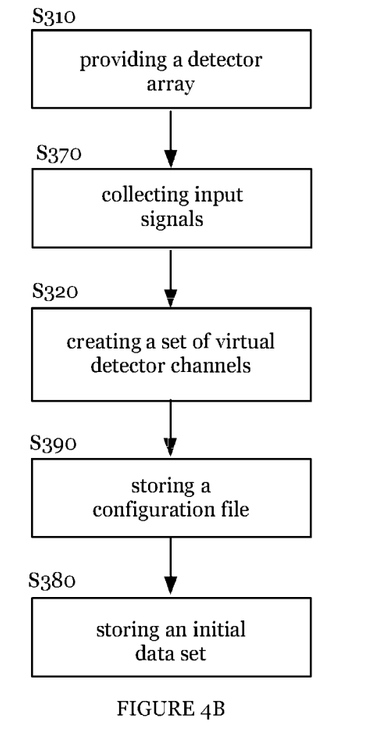
Figure 5A:
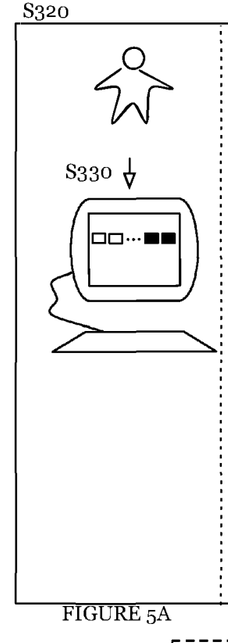
Figure 5B:
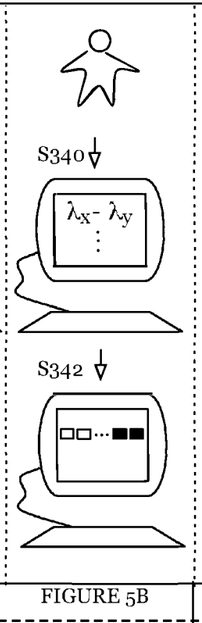
Figure 5C:
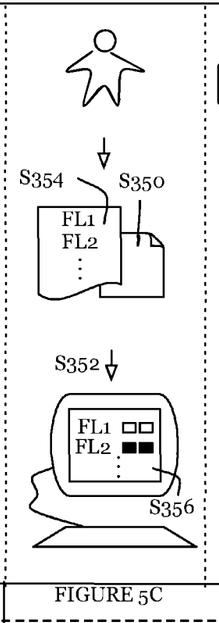
Figure 5D:
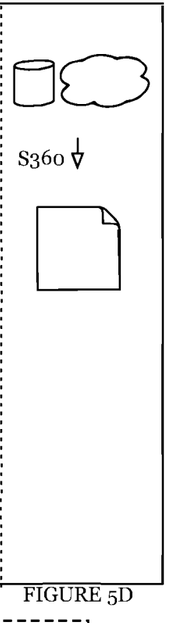
Figure 5E:
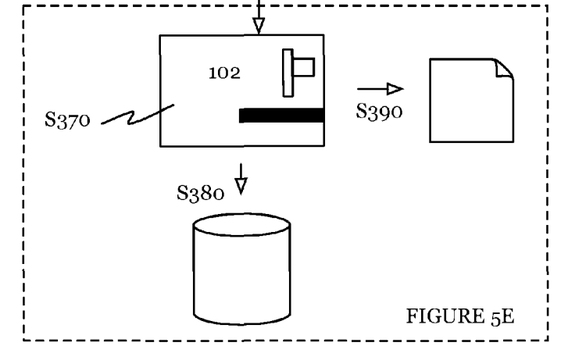
Figure 6A:
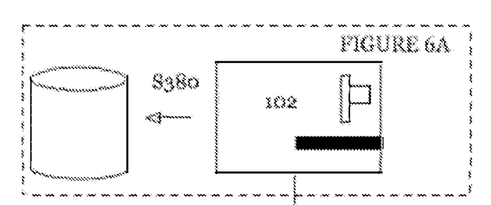
Figure 6B:
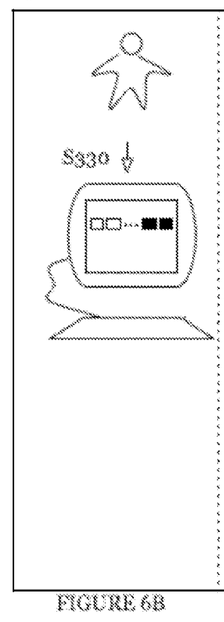
Figure 6C:
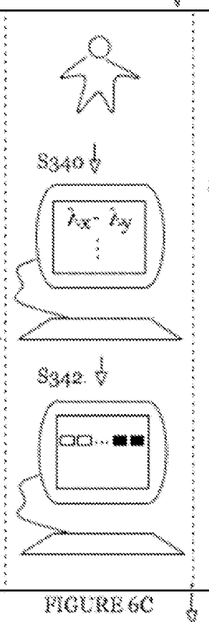
Figure 6D:
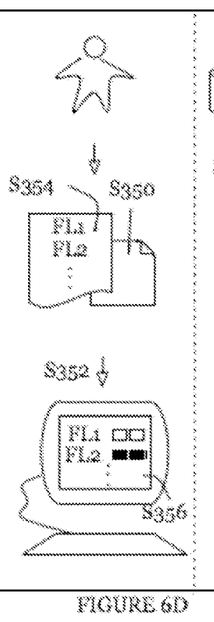
Figure 6E:
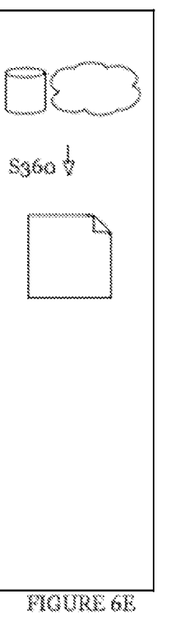
Figure 6F:
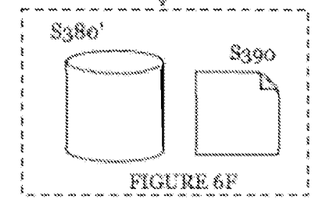

The user interface for a flow cytometer is used to enable the grouping of detector signals to form virtual detector channels through which data is collected and organized. As shown in FIGS. 4A and 4B, in preferred embodiments, the user interface provides a method for collecting a data set for a flow cytometer sample in a flow cytometer including the steps of: providing a detector array 8310 having a plurality of detectors that collectively detect a full spectral range of input signals from the flow cytometer, in which each detector detects a subset spectral range of the full spectral range; creating a set of virtual detector channels 8320 by grouping detectors in the detector array, and collecting the full spectral range of input signals 8370 from the flow cytometer sample with the detector array. Each virtual detector channel corresponds to a detector group and has a virtual detector channel range that includes the sum of subset spectral ranges of the detectors in the corresponding detector group. The step of creating a set of virtual detector channels 8320, which may include one or more of several variations of substeps, may be performed before and/or after the step of collecting input signals 8370. The method may further include storing an initial data set based on the collected input signals 8380 and/or storing a configuration file of the configuration of the virtual detector channels 8390. The user interface enables extraction of data from a flow cytometer system having the optical and/or detection systems as described above, or any suitable instrument having an array of multiple detectors that each detects a portion of a full spectrum of light input signals. The user interface enables a more comprehensive collection of data, and simplifies the process for setting up and configuring the detector system of the flow cytometer. However, the user interface and method for collecting a data set may alternatively be used in any suitable system requiring detection of a substantial spectrum of signals, such as microscopy.

The step of providing a detector array 8310 preferably includes providing a system that detects known subsets of an entire light (e.g., fluorescence) spectrum detected by the flow cytometer. The detector array is preferably similar to the detection system described above and shown in FIGS. 2 and 3, but may alternatively be any suitable detection system. In particular, the detector array includes separate individual detector devices that detect a dispersed full spectrum of light such that adjacent detectors may detect portions or subset spectral ranges of the full spectrum of light, and more preferably such that adjacent detectors detect contiguous subset spectral ranges of the full spectrum of light. For example, within a group of adjacent detectors in the detector array, each detector may detector light in 10 nm increments, such that a first detector may detect light having a wavelength of approximately 491-500 nm, a second middle detector may detect light having a wavelength of approximately 501-510 nm, and a third detector may detect light having a wavelength of approximately 511-521 nm. The detector array may include photodiodes, phototransistors, or any suitable kind of light detector.

The step of creating a set of virtual detector channels 8320 functions to organize the signals collected by detectors in the detector array into designated data channels. As best shown in FIG. 3, creating a set of virtual detector channels 8320 includes grouping detectors in the detector array 8322. Each virtual detector channel 240a, 240b, 240c and 240d corresponds to a detector group and has a virtual detector channel range that includes the sum of the subset spectral ranges of the detectors in the corresponding detector group. In other words, each virtual detector channel 240a, 240b, 240c and 240d includes the summed or combined input signals collectively detected by the individual detectors in the detector group corresponding to the virtual detector channel. One or more detector groups may include detectors that are physically contiguous with each other (e.g., a "block" of detectors and/or detect contiguous subset spectral ranges of light, such that the corresponding virtual detector channel range collects light of a continuous spectral range (as in virtual detector channels 240a, 240b, and 240d). Furthermore, one or more detector groups may include detectors that are not physical contiguous with each (e.g., a "split block" of detectors) and/or detect not contiguous subset spectral ranges of light, such that the corresponding virtual detector channel range collects light of a discontinuous spectral range, as in virtual detector channel 240c.

The step of collecting the full spectral range of input signals 8370 functions to gather raw data with the detector array. Collecting input signals 8370 may include collecting a full dynamic range of input signals that provides at least a 1:100,000 ratio, and more preferably at least a 1:1,000,000 ratio, between the faintest signals and the brightest signals from the flow cytometer sample. In a preferred embodiment, the data is collected in a raw, unmodified format without adjustment in gain level of the detectors, but may be collected in any suitable manner.

As shown in FIGS. 5 and 6, the step of creating a set of virtual detector channels S320 may be performed before and/or after the step of collecting input signals S370, such as before and/or after performing a sample run on the flow cytometer. In a first preferred embodiment, the step of creating a set of virtual detector channels S320 is performed before collecting input signals. As shown in FIG. 5A, in a first variation of this embodiment, the step of creating a set of virtual detector channels S320 includes receiving a user selection of detector groups S330 in which the user manually enters or indicates detector groups that make up the detector channels. For example, each detector may be labeled or numbered, and the user may specify that detectors "x" through "y" is a detector group. Since each detector is designated for detecting a particular subset spectrum range of input signals, the user selection of detector groups in turn creates virtual detector channels corresponding to the detector groups. For a flow cytometer system having multiple lasers, the user may further specify which laser is assigned to each detector, detector group, and/or virtual detector channel.

As shown in FIG. 5B, in a second variation of the first preferred embodiment, the step of creating a set of virtual detector channels S320 includes receiving a user selection of desired virtual detector channel ranges S340 (or summed subset spectrum ranges of input signals) and grouping detectors into detector groups that correspond to the selection of virtual detector channel ranges S342, thereby forming a set of virtual detector channels that define the desired virtual detector channel ranges. For example, the user may specify a range of wavelengths, such as that between wavelength "a" and wavelength "b", to assign to a particular virtual detector channel, and the user interface may automatically correlate the range of wavelengths to specific individual detectors, by determining which individual detectors to group together to form a virtual detector channel that detects light between wavelengths "a" and "b". In some embodiments, the user interface may automatically exclude certain detectors from any detector group or virtual detector channel, such as in scenarios in which lasers in the optical system are active.

As shown in FIG. 5C, in a third variation of the first preferred embodiment, the step of creating a set of virtual detector channels 8320 includes receiving one or more configuration parameters 8350 and optimally grouping detectors based on the configuration parameters 8352. In an example of this variation, the step of creating a set of virtual detector channels includes receiving a user selection of a set of fluorochromes 8354 that tag a flow cytometer sample, determining an optimal detector group for each fluorochrome based on at least one configuration parameter, and assigning the optimal detector group to each fluorochrome 8356 and thereby providing a virtual detector channel for each fluorochrome. Between different sample runs and/or sets of fluorochromes, the detector groups may be reassigned to provide different suitable virtual detector channels for different applications. Optimally grouping detectors 8352 may be dependent on one or more of several configuration parameters, including: minimizing spillover (overlapping detection of a fluorochrome between multiple detector channels), simplifying requirements for spillover compensation (typically algorithms to compensate for spillover in the data), instrument-specific calibration parameters, maximizing sensitivity of the detector channels (such as based on previous sample runs with a particular set of fluorochromes), any suitable configuration parameter based on the user-selected set of fluorochromes or instrumentation, or any suitable parameter. Optimally grouping detectors 8352 is preferably performed automatically by the user interface, but may additionally and/or alternatively be performed manually by the user. The user interface and/or user may further determine the optical laser configuration in the flow cytometer for each fluorochrome.

As shown in FIG. 5csD, in a fourth variation of the first preferred embodiment, the step of creating a set of virtual detector channels 8320 includes receiving a configuration file 8360 that defines a predetermined group of detectors, arrangement of virtual detector channels, laser configuration, and/or any suitable settings for the flow cytometer system. In this variation, the step of grouping the detectors preferably incorporates the settings in the configuration file, and/or may include further modifications by the user or system. The configuration file may be directly provided by the user such as on portable media, selected from the user interface, selected and downloaded from a network or server, provided in a machine-read sample label such as a bar code, or by any suitable means. The configuration file may be a saved configuration file from a previous sample run from the same or different flow cytometer system or other instrument, or may be a template configuration file. A configuration file defining the virtual detector channel settings and/or other instrument settings may help increase usability of the instrument, and help ensure consistency in analysis for similar experiments or tests. This consistency in analysis for similar experiments or tests may be particularly important in some applications, such as clinical applications.

In a second preferred embodiment, the step of creating a set of virtual detector channels 8320 is performed after collecting input signals 8370 (such as after a sample run with the flow cytometer system). As shown in FIGS. 6B and 6C, in first and second variations of this embodiment the step of creating a set of virtual detector channels 8320 include receiving a user selection of detector groups 8330 and receiving a user selection of desired virtual detector channel ranges 8340, respectively, similar to the first and second variations of the first preferred embodiment.

As shown in FIG. 6D, in a third variation of this embodiment, the step of creating a set of virtual detector channels 8320 includes receiving one or more configuration parameters 8350 and optimally grouping detectors based on the configuration parameters 8352, similar to the third variation of the first embodiment. Furthermore, the user interface may additionally and/or alternatively optimize the detector grouping based on bright and/or dim (or blank) peaks of a multi-intensity flow cytometer sample, which may be identified automatically by the user interface and/or manually by the user. This optimization may occur after a sample run, or after the user runs a set of experimental controls but before the actual sample run.

As shown in FIG. 6E, in a fourth variation of the second preferred embodiment, the step of creating a set of virtual detector channels 8320 includes receiving a configuration file 8360, similar to the fourth variation of the first preferred embodiment.

Although the step of creating a set of virtual detector channels S320 is preferably one of the above variations, in other embodiments the step of creating a set of virtual detector channels S320 may be any suitable combination or permutation of the above variations and/or any suitable processes for forming virtual detector channels. For example, one or more of the variations of creating a set of virtual detector channels of the first embodiment may be implemented in some manner after the step of collecting input signals. Similarly, one or more of the variations of creating a set of virtual detector channels of the second embodiment may be implemented in some manner before the step of collecting input signals. Furthermore, through the user interface or other means, the virtual detector channels may be created in multiple configurations for a single sample run (e.g. in a first configuration before collecting the input signals and in a second configuration, different from the first configuration, after collecting the input signals) and/or between different instances of sample runs (e.g. in a first configuration for one sample run and in a second configuration, different from the first configuration, for another sample run).

As shown in FIGS. 4-6, the user interface may further enable storing the collected input signals from most, if not all, available detectors. Storing the collected input signals may include storing an input signal as the signal individually collected by each separate detector in the detector array S380 (e.g., FIG. 6A), and/or may include storing the input signal as the signal collected by each separate detector group through the virtual detector channel S380' (e.g., FIG. 6F). The data set of collected input signals may be saved to a local memory, portable media, server, network or any suitable memory. The stored data set preferably includes the full spectral range of the detectors, but may include any suitable portion of the spectral range or collected signals. The stored data set may also be useful for analysis and other manipulations, as described in U.S. Pat. No. 7,996,188 entitled "User interface for a flow cytometer", which is incorporated in its entirety by this reference.

As shown in FIGS. 4-6, the user interface may further enable storing a configuration file S390 that defines a predetermined grouping of detectors, arrangement of virtual detector channels, laser configuration, and/or any suitable settings for the flow cytometer system. The step of storing the configuration file S390 may include saving to a local memory or portable media, saving to a server or network, or any suitable saving step. The stored configuration file may be used for future sample runs, as described above, and/or as a template. Multiple configuration files may be stored. For example, a first configuration file may be stored immediately after a sample run to save an initial configuration of detector groups and virtual detector channels, and a second configuration file may be stored after optimizing the grouping based on characteristics of the collected data. In this example, the first and second configuration files may be compared or analyzed for future reference. The user interface may additionally and/or alternatively include exporting the configuration file to a different medium, such as a printout.

As a person skilled in the art will recognize from the previous detailed description and from the figures and claims, modifications and changes can be made to the preferred embodiments of the invention without departing from the scope of this invention defined in the following claims.

The invention claimed is:

1. A light detection component comprising:
   a plurality of user-configurable groups of photodetectors; and
   a plurality of detector channels, wherein each detector channel is assigned to one or more of the user-configurable groups of photodetectors;
   wherein the photodetectors comprise an array of photodetectors, wherein the array of photodetectors:
   is configured to detect light from 400 nm to 900 nm;
   comprises 50 or more photodetectors that each detect light in 10 nm increments; and
   the spectral range of each photodetector in the array overlaps with adjacent photodetectors.

2. The light detection component according to claim 1, wherein the light detection system is configured to:
   detect light from a sample irradiated with a light source; and
   generate a data signal from the detected light.

3. The light detection component according to claim 2, wherein the light detection system is configured to assign each detector channel to a user-configurable group of photodetectors before generating a data signal from the light detected from the irradiated sample.

4. The light detection component according to claim 2, wherein the light detection system is configured to assign each detector channel to a user-configurable group of photodetectors after generating a data signal from the light detected from the irradiated sample.

5. The light detection component according to claim 2, wherein each data signal is collected using a different detector channel.

6. The light detection component according to claim 1, wherein the photodetectors comprise a linear array of photodetectors.

7. The light detection component according to claim 1, wherein the photodetectors comprise an array of photodiodes.

8. The light detection component according to claim 1, wherein the photodetectors comprise an array of phototransistors.

9. The light detection component according to claim 1, wherein the light detection system further comprises an amplifier circuit comprising a plurality of amplifiers configured to convert current from each detector channel into a voltage output signal.

10. A system comprising:
   a light source for irradiating a sample in a flow stream; and
   a light detection component comprising:
      a plurality of user-configurable groups of photodetectors; and
      a plurality of detector channels, wherein each detector channel is assigned to one or more of the user-configurable groups of photodetectors;
   wherein the photodetectors comprise an array of photodetectors, wherein the array of photodetectors:
   is configured to detect light from 400 nm to 900 nm;
   comprises 50 or more photodetectors that each detect light in 10 nm increments; and
   the spectral range of each photodetector in the array overlaps with adjacent photodetectors.

11. The system according to claim 10, wherein the light detection component is configured to:
   detect light from an irradiated sample; and
   generate a data signal from the detected light.

12. The system according to claim 11, wherein the system is configured to assign each detector channel to a user-configurable group of photodetectors before generating a data signal from the light detected from the irradiated sample.

13. The system according to claim 11, wherein the system is configured to assign each detector channel to a user-configurable group of photodetectors after generating a data signal from the light detected from the irradiated sample.

14. The system according to claim 11, wherein each data signal is collected using a different detector channel.

15. The system according to claim 10, further comprising a light dispersion component configured to disperse a spectrum of light onto the plurality of photodetectors.

* * * * *